United States Patent [19]
Anderson

[11] Patent Number: 5,267,972
[45] Date of Patent: Dec. 7, 1993

[54] HYPODERMIC SYRINGE WITH NEEDLE GUARD

[76] Inventor: Wayne W. Anderson, 273 Milton Ave., San Bruno, Calif. 94066

[21] Appl. No.: 915,531

[22] Filed: Jul. 20, 1992

[51] Int. Cl.⁵ ............................................. A61M 5/32
[52] U.S. Cl. ..................................... 604/192; 604/198
[58] Field of Search ............... 604/198, 192, 187, 263, 604/110, 111

[56] References Cited
U.S. PATENT DOCUMENTS 4,416,663  11/1983  Hall ..................................... 604/198
4,475,903  10/1984  Steenhoisen et al. ................ 604/111
4,643,199   2/1987  Jennings, Jr. ......................... 604/198
4,911,693   3/1990  Paris ................................... 604/198 X
4,966,592  10/1990  Burns et al. ....................... 604/263 X

*Primary Examiner*—John D. Yasko
*Attorney, Agent, or Firm*—Linval B. Castle

[57] ABSTRACT

A hypodermic syringe with cylindrical guard that surrounds the needle and its tip at all times will protect medical personnel from possible injury from contaminated needles. The needle guard retracts into a cylindrical cavity when pressed against a patient and extends by a spring when the needle is withdrawn.

8 Claims, 1 Drawing Sheet

U.S. Patent
Dec. 7, 1993
5,267,972
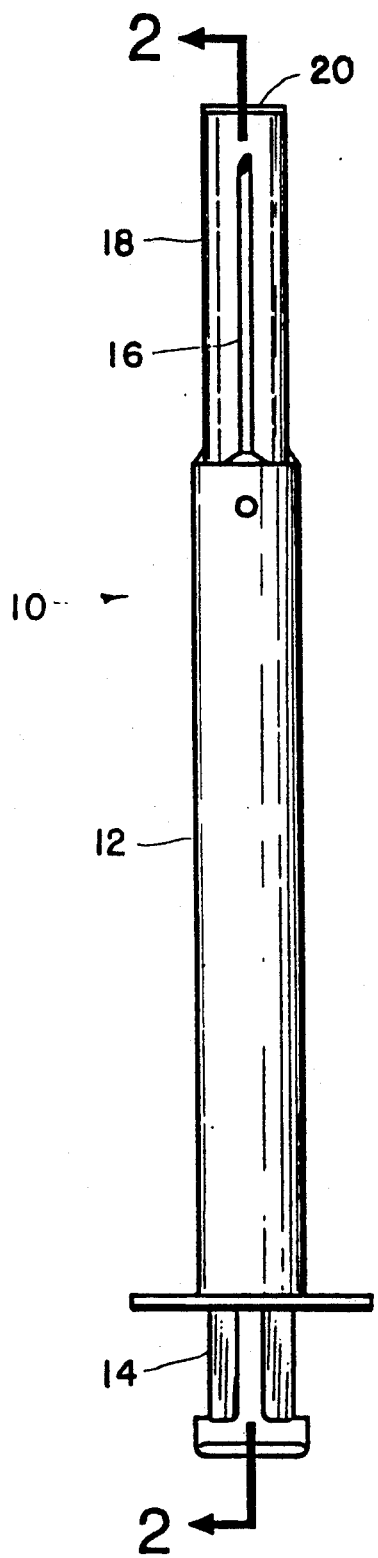
Figure 1
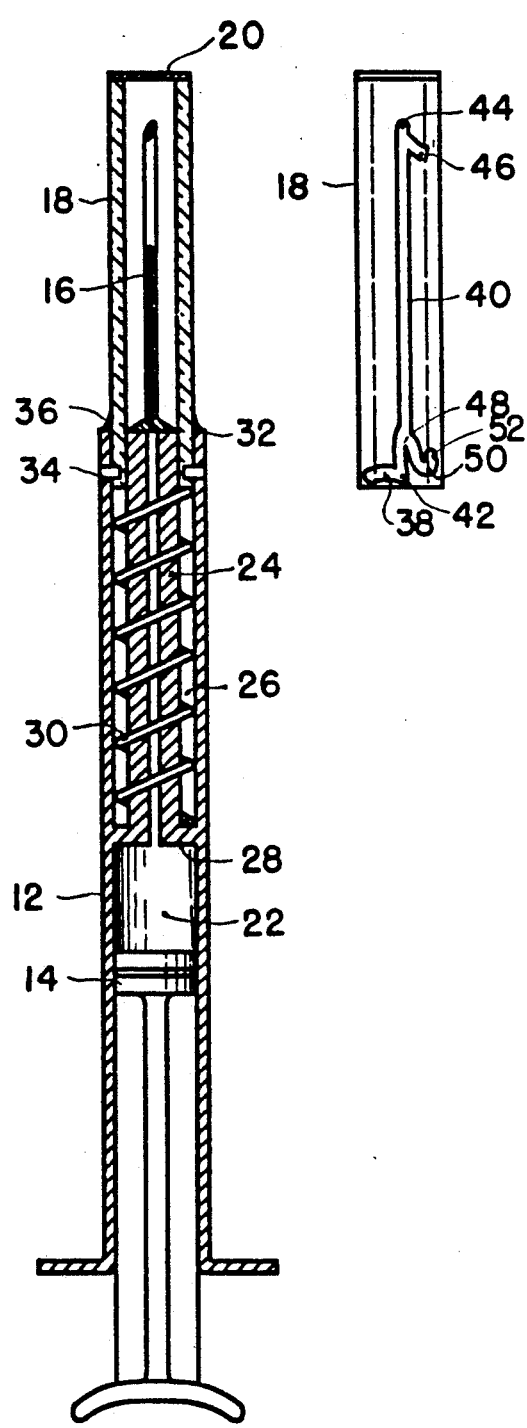
Figure 3
Figure 2

HYPODERMIC SYRINGE WITH NEEDLE GUARD

BACKGROUND OF THE INVENTION

This invention relates to medical syringes and particularly to a syringe containing a spring biased receding guard that surrounds the needle and its tip before and after use.

It is well known that used syringe needles are a source of harmful bacteria and that hospitals and medical offices destroy every needle after only a single use. Unfortunately, there are instances where a physician or technician, after administering an injection or withdrawing a blood specimen from a patient, has merely scratched himself or herself with the used needle and has thus contracted a disease that could result in a serious illness of even an untimely death. Paramedics forced to administer fast emergency first aid care under poor conditions are particularly susceptible to receiving a scratch from a contaminated needle dislodged by the thrashing of an accident victim.

The hypodermic syringe to be described employs a conventional needle but it is completely shielded by a plastic tube that recedes against the bias of a spring into cylindrical cavity in the syringe barrel while the needle is in use. The plastic tube or guard has a thin diaphragm seal at its end to assure the sterile integrity of the needle.

BRIEF DESCRIPTION OF THE DRAWINGS

In the drawings which illustrate the preferred embodiment of the hypodermic syringe of the invention:

FIG. 1 is a side view of the syringe;

FIG. 2 is a sectional view taken along the lines 2—2 of FIG. 1; and

FIG. 3 is a side view of the transparent guard and illustrates guide tracks on the exterior surface thereof.

DETAILED DESCRIPTION OF THE PREFERRED EMBODIMENT

As illustrated in FIG. 1, the syringe 10 includes a barrel 12 having at one end a conventional piston 14 entering the barrel and, at the opposite end, a conventional hypodermic needle 16 of appropriate size and length.

The preferred embodiment also includes a plastic needle guard 18 the distal end 20 of which is covered and sealed with a thin plastic end sheet to preserve the sterilization of the needle 16. The needle guard 18 is intended to remain around the needle and upon pressure of the end 20 against the skin of a patient or the seal of a bottle of injectable medication, the needle will pierce the end sheet and the tubular guard 18 will retract into a cylindrical cavity in the barrel 12. Upon extraction of the needle 16, the end 20 will remain in contact with the patient, or seal, while the needle guard 18 slides from the cylindrical cavity, urged by the bias from a spring.

FIG. 2 is a sectional view of the syringe 10 taken along the lines 2—2 of FIG. 1. It will be noted that fluid in the fluid reservoir 22 within the barrel 12 is coupled through a tube 24 having a small diameter bore to the needle 16 attached to the end surface thereof. The exterior surface of the tube 24 is spaced from the interior surface of the barrel to form a cylindrical cavity 26 that is sealed off from the reservoir by the circular wall 28 and is open at the distal end. A thin helical compression spring 30 is housed in the cylindrical cavity 26.

The plastic needle guard 18 has a diameter and wall thickness that will enable it to slide into the cylindrical cavity 26 and is mounted so that the end is about a half inch within the cavity. Mounted in holes diametrically bored through the housing 12 near its end 32 are two pins 34 that extend through the wall of the housing and about half way into the wall of the plastic needle guard 18. The needle guard 18 is thus secured to the body of the syringe 10. An air tight seal between the cylindrical cavity 26 and the exterior is provided by a plastic sealant 36 around the end surface of the barrel 12 and adhering to the surface of the needle guard 18.

The pins 34 extending through the housing 12 and partially into the wall of the needle guard 18 do not enter into holes in the needle guard but enter at an initial point 38 in slots 40 formed in the exterior surface of the needle guard as shown in FIG. 3.

FIG. 3 illustrates the exterior surface of one side of the needle guard 18 with the approximate location and pattern of various slots which, guided by the pins 34, control both the rotational and longitudinal placement of the guard 18. Identical slots are in the opposite exterior surface of the guard.

As mentioned above, initially the pins 34 are at a point 38 in opposite surfaces of the guard which, sealed by the sealant 36 to the barrel 12, is temporarily locked to the barrel. When the syringe 10 is to be used the guard 18 is manually rotated slightly toward the left or counterclockwise thereby breaking the sealant 36 and moving the pins 34 to point 42 in the slots. At this point the guard is free to move longitudinally along the slot 40.

If the reservoir 12 in the syringe 10 has been precharged with the proper injectable and dosage, the syringe may now be aspirated and the needle 16 inserted into the patient, puncturing the plastic seal at the end 20 of the guard and driving the guard 18 into the cylindrical cavity 26 against the slight bias of the spring 30 in the process. In the more likely situation in which a sterile syringe 10 requires charging with a particular injectable and dosage, the end 20 of the guard with its intact plastic seal is pressed against the seal of the injectable container so that the needle will puncture the end seal to enter the container and the guard 18 will retract into the cylindrical cavity 26 with the pins 34 sliding along the slots 40. If desired, the guard 18 may be locked in the cavity 26 with the needle 16 exposed by merely a slight counterclockwise manual rotation of the guard 18 so that the pins 34 are moved from the retraction position 44 a short distance along a downward and outward slanted slot to a locked position 46 as shown in FIG. 3. To remove the guard from this locked position, it is only necessary to slightly push the guard back into the cavity 26 so that the pins 34 are driven back to their retraction position 44 where the pins may then return through the slot 40 to permit the guard to cover the needle.

When the guard 18, driven by the bias of spring 30, is nearly fully extended and covering the needle, the pins 34 encounter a branch 48 in the slot. A slight clockwise urging of the guard will restore the guard to its original position with the pins at point 42 where the guard may again be retracted. The slots at the branch 48 are constructed so that, without the slight clockwise urging, the pins will normally enter the opposite branch to cause the guard to slightly rotate counterclockwise and come to rest at slot points 50. From point 50 the slot makes a sharp upturn to the point 52 so that any accidental inward force against the end 20 and parallel with the longitudinal axis of the guard 18 will move the guard so that the pins enter points 52 to halt further inward longitudinal movement. The slot points 50 and 52 therefore become self-locking positions which assures that the plastic needle guard 18 will continuously protect medical personnel from possible injury from a contaminated needle.

I claim:

1. A hypodermic syringe with needle guard comprising:
   an elongated tubular barrel having first and second ends, said barrel containing a fluid reservoir and means for pumping fluid to and from said reservoir;
   a conduit within said barrel and spaced therefrom for axially connecting said reservoir with a hypodermic needle axially secured to said conduit and extending from the first end of said barrel, the space between said conduit and the interior surface of said barrel forming a cylindrical cavity having its opening adjacent said first end of said barrel;
   a tubular needle guard having first and second ends, said guard surrounding the exterior surface of said hypodermic needle and extending past the tip thereof, the size of said needle guard permitting the sliding of said guard within said cylindrical cavity; and
   control means including a longitudinal guide groove in the exterior surface of said needle guard, said control means including a control pin extending through a radial hole in said barrel and engaging said guide groove for preventing removal or said guard from said cavity.

2. The hypodermic syringe claimed in claim 1 further including spring means within said cylindrical cavity for urging said needle guard from said cavity.

3. The hypodermic syringe claimed in claim 2 further including a first seal over the first end of said needle guard, said seal to be broken by the tip of said hypodermic needle.

4. The hypodermic syringe claimed in claim 3 further including a second seal between the first end of said tubular barrel and the cylindrical surface of said needle guard, said seal to be broken by slight manual rotation of said guard.

5. The hypodermic syringe claimed in claim 1 wherein said control means pin engages a circumferential portion of said guide groove adjacent the second end of said tubular needle guard for preventing longitudinal movement of said guard.

6. The hypodermic syringe claimed in claim 5 wherein said control means pin is rotatable from an initial position in a circumferential portion of said guide groove adjacent said second end of said needle guard to a vertical portion of said guide groove to enable longitudinal movement of said guard within said cylindrical cavity.

7. The hypodermic syringe claimed in claim 6 further including a portion of guide groove adjacent the first end of said needle guard having a circumferential component for said pin to temporarily lock said guard completely within said cylindrical cavity.

8. The hypodermic syringe claimed in claim 6 further including a section of guide groove branching from a longitudinal groove near the second end of said needle guard and terminating in a circumferential portion having a short longitudinal segment for entrapment of said pin and the temporarily locking of said needle guard to said barrel.

* * * * *